United States Patent [19]

Norman

[11] Patent Number: 5,008,415
[45] Date of Patent: Apr. 16, 1991

[54] VOLATILE FLUORINATED β-KETOIMINES AND ASSOCIATED METAL COMPLEXES

[75] Inventor: John A. T. Norman, Whitehall, Pa.

[73] Assignee: Air Products and Chemicals, Inc., Allentown, Pa.

[21] Appl. No.: 411,275

[22] Filed: Sep. 22, 1989

Related U.S. Application Data

[63] Continuation-in-part of Ser. No. 270,719, Nov. 14, 1988, Pat. No. 4,950,790.

[51] Int. Cl.$^5$ .............. C07F 1/08; C07F 15/06; C07F 7/08; C07F 7/18
[52] U.S. Cl. ................................. 556/32; 556/33
[58] Field of Search ............................. 556/32, 33

[56] References Cited

U.S. PATENT DOCUMENTS

| | | | |
|---|---|---|---|
| 3,356,527 | 12/1967 | Moshier et al. | 117/107.2 |
| 3,594,216 | 6/1969 | Charles et al. | 117/107.2 |
| 4,264,494 | 4/1981 | Grychtol | 556/32 X |
| 4,552,972 | 11/1985 | Aratani et al. | 556/32 X |
| 4,654,053 | 3/1987 | Sievers et al. | 55/68 |
| 4,734,515 | 3/1988 | Bitterli et al. | 556/32 |
| 4,861,904 | 8/1989 | Sugie | 556/32 |

OTHER PUBLICATIONS

B. J. Aylett et al., "Chemical Vapour Deposition of Metal Silicides from Organometallic Compounds with Silicon-Metal Bonds," Vacuum, vol. 35, Nos. 10–11, pp. 435–439, 1985.
P. J. Wright et al., "MOCVD Layer Growth of ZnSe Using a New Zinc Source", Paper Accepted for Publication in J. of Crystal Growth, London (1986).
A. E. Martell et al., "Influence of Fluorine Substitution on the Properties of Metal Chelate Compounds-II", J. Inorg. Nucl. Chem., vol. 5, pp. 170–181, (1958).
M. F. Richardson and R. E. Sievers, "Schiff Bases Prepared from Ethylendiamine and Hexafluoroacetylacetone", J. Inorgan. Nucl. Chem., vol. 32, pp. 1895–1906 (1970).
D. A. Johnson et al., "Synthesis and Crystal Structure of 1,1,1,5,5,5-Hexafluoro-2-Aminopenton-4-One (HFAP)", J. Fluorine Chem., 27, (1985) 371–378.

Primary Examiner—Paul F. Shaver
Attorney, Agent, or Firm—Mark L. Rodgers; William F. Marsh; James C. Simmons

[57] ABSTRACT

Fluorinated β-ketoimine ligands and highly volatile β-ketoiminato metal complexes of the ligands are synthesized by silylating a fluorinated β-diketone to form a silylenolether, and subsequently reacting the silylenolether with a primary amine to form the desired ligand having the structural formula:

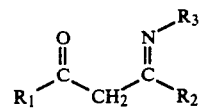

wherein $R_1$ and $R_2$ are independently linear or branched perfluorinated, $C_1$–$C_8$ alkyl groups and $R_3$ is a phenyl or $C_1$–$C_8$ alkyl, hydroxyalkyl, or ether group, all of which can be partially or fully fluorinated. The corresponding metal complex is formed by treating the ligand with a metal halide.

7 Claims, No Drawings

VOLATILE FLUORINATED β-KETOIMINES AND ASSOCIATED METAL COMPLEXES

CROSS-REFERENCE TO RELATED APPLICATION

This application is a continuation-in-part of co-pending application Ser. No. 07/270,719, filed Nov. 14, 1988, now U.S. Pat. No. 4,950,790.

TECHNICAL FIELD

The present invention relates to fluorinated organic ligands and volatile metal complexes formed from such ligands.

BACKGROUND OF THE INVENTION

In the electronics industry there is a growing need for volatile sources of different metals to be used in the chemical vapor deposition (CVD) of metallic films, metal oxide films, metal silicide films, and the like. The key property required for such metal sources is that they readily evaporate or sublime to give a metal containing vapor or gas which can be decomposed in a controlled manner to deposit a film onto a target substrate. Examples of such materials which are commonly utilized in the microelectronics industry in the preparation of printed circuits and semiconductor devices include the complex $H_3SiCo(CO)_4$ complex which is pyrolyzed in the gas phase at 670°–770° K. to produce CoSi and dimethylzinc (1,4 dioxane) which is reacted with hydrogen selenide at 250°–550° C. to produce ZnSe. References teaching the above CVD methods are B.J. Aylett, et al in Vacuum, 35 p 435–439(1985) and P.J. Hright, et al., in a paper accepted for publication in J. of Crystal Growth, London (1986), respectively.

Known fluorinated metal complexes that are chemically stable and easily volatized into the gas phase are the perfluorinated β-diketone metal coordination compounds along with their parent β-diketone precursor ligands, represented by the formulas:

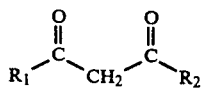  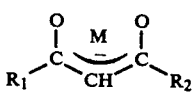

Ligand    Metal Coordination Compound wherein $R_1$ is alkyl or fluoroalkyl, $R_2$ is fluoroalkyl, and M is a metal capable of forming a coordination compound. The volatility and gas phase stability of these compounds have been exploited for the gas chromatographic separation of various metals, the purification of uranium and the manufacture of specialty glasses. Decomposing such metal complexes by reaction with hydrogen in the gas phase to deposit thin metal films is taught in U.S. Pat. No. 3,356,527.

In the past, attempts have been made to condense primary amines or primary diamines with ligands similar to those having the above structure. In instances in which $R_1$ and $R_2$ are not both fluorocarbon groups, it was reported that an O atom could be replaced with a N atom from an amine by direct Schiff-base condensation between an appropriate β-diketone and an amine. Additionally, the corresponding metal complex could be synthesized by chelation to a metal ion. See A.E. Martell, et al J. Inorg. Chem. Vol. 5 pp 170–181 (1958).

Sievers, et al. reported in J. Inorg. Nucl. Chem. Vol 32 pp 1895–1906 (1970), that ligands in which $R_1$ and $R_2$ are both perfluoroalkyl and in which an oxygen has been replaced with an amine have not been obtainable. It is believed that such methods have been unsuccessful because the perfluorinated β-diketones are of such high acidity that the amine used the reaction becomes protonated. thereby forming a salt between the amine and the β-diketone rather than forming the desired ligand. Sievers, et al do report synthesizing a ligand having the structure:

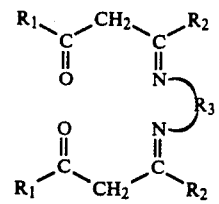

wherein $R_1=R_2=CF_3$ and $R_3=-CH_2CH_2-$. This ligand was reportedly synthesized by sublimation of the salt $[(CF_3C(O)CHC(O)CF_3)]_2^-[NH_3-CH_2CH_2-NH_3]^{+2}$. The ligand was reported to be chemically unstable and hence impossible to isolate.

In U.S. Pat. No. 4,654,053 Sievers. et al. teach a process for separating gaseous oxygen from a multi-component gas stream using a wide range of Schiff base metal chelates, including those containing perfluoro moieties. No special synthesis techniques are taught, however, for making the perfluoro compounds.

Charles, U.S. Pat. No. 3,594,216 discloses a process for depositing a metallic coating on a substrate by heating the substrate and contacting it with vaporized metal-organic beta-ketoamine chelates. The metal-organic beta-ketoamines were prepared by conventional synthesis techniques. While a wide range of metal chelates are disclosed generally, none of the examples or synthesis techniques specifically use perfluorinated metal chelates.

Johnson, et al in Journal of Fluorine Chemistry, 27 pp 371–378 (1985) reported synthesizing a ligand in which $R_1$ and $R_2$ are perfluoroalkyl and oxygen was replaced with an ammonia nitrogen. The $Cu^{+2}$ complex was also prepared and was reported to be volatile.

BRIEF SUMMARY OF THE INVENTION

The present invention is a class of novel, β-ketoimine ligands and highly volatile metal complexes of the ligands and also a process for making the same. The β-ketoimine ligands of the present invention are those of the general structural formula:

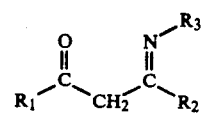

wherein $R_1$ and $R_2$ are independently linear or branched, perfluorinated, $C_1$–$C_8$ alkyl groups, and $R_3$ is any suitable organic functionality such as a phenyl or $C_1$–$C_8$ alkyl, hydroxyalkyl or ether group, all of which can be partially or fully fluorinated.

The highly volatile β-ketoiminato metal complexes which are synthesized from these ligands have the structural formula:

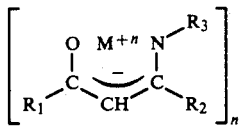

wherein $R_1$, $R_2$ and $R_3$ are as described above, and M is a metal, and n is 1, 2 or 3.

The present invention is also a process for making both the β-ketoimine ligands and metal complexes described above. The ligands are synthesized by silylating a fluorinated B-diketone to form a silylenolether, and subsequently reacting the silylenolether with a primary amine to form the desired ligand. The corresponding metal complex is formed by treating the resulting ligand with potassium methoxide followed by treatment with a halide salt of the desired metal.

DETAILED DESCRIPTION OF THE INVENTION

The present invention is a class of heavily fluorinated β-ketoimine ligands and thermally volatilizable B-ketoiminato metal complexes of the ligands. The ligands are characterized in that they are highly fluorinated and contain oxygen and nitrogen donor atoms which can be covalently coordinated to a central metal atom to form the corresponding metal complex. This class of ligand. as well as the corresponding metal complex, are chemically stable and easily volatized into the gas phase. The high fluorine content of the complex is believed to reduce the Van der Waals forces between individual molecules and hence lower the boiling or sublimation point of the compound.

The heavily fluorinated β-ketoimine ligands of the present invention can be represented by the structural formula:

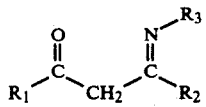

I wherein $R_1$ and $R_2$ are independently linear or branched, perfluorinated. $C_1$–$C_8$ alkyl groups, and $R_3$ is any suitable organic functionality for example, a phenyl or $C_1$–$C_8$ alkyl, hydroxylalkyl or ether group, all of which can be partially or fully fluorinated.

The highly volatile metal complexes which are synthesized from these ligands can be represented by the structural formula:

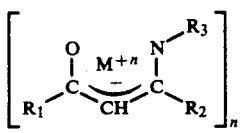

II wherein $R_1$, $R_2$ and $R_3$ are as described above, and M is a metal and n=1, 2 or 3. These volatile complexes hold great potential for use as metal sources in Chemical Vapor Deposition (CVD) processes engaged in the art of depositing, for instance, metal films or metal oxide films.

The ligands of structure I above are synthesized by treating a fluorinated β-diketone of the formula $R_1COCH_2COR_2$ with potassium hydride under anhydrous conditions to produce a compound of the formula $R_1COCHCOR_2^-K^+$ and subsequently reacting the resultant $R_1COCHCOR_2^-K^+$ with a silylchloride such as, t-butyldimethylsilylchloride. to produce a silylenolether having the general formula:

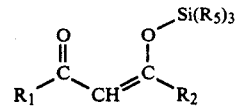

wherein $R_1$ and $R_2$ are as described above, and each $R_5$ is an alkyl group. The silylenolether described above is then treated with a primary monoamine, $R_3NH_2$ wherein $R_3$ is as above to produce the desired β-ketoimine ligand of structural formula I; i.e. $R_1COCH_2CN(R_3)R_2$.

To form the metal complex of the β-ketoimine ligand formed above, the ligand is initially treated with potassium methoxide to produce a compound of the formula $R_1COCHCN(R_3)R_2^-K^+$, which is subsequently treated with a metal halide of the formula $M^{+n}(X)_n$, where n=1, 2 or 3, and X is a halogen, to form the desired highly fluorinated β-ketoiminato complex of formula II above.

The ligands of formula I produced in accordance with this invention can exist in two tautomeric forms, enol and keto, with the keto form being represented generally by formula I. Preferred ligands and metal complexes of the present invention include:

Ligands.

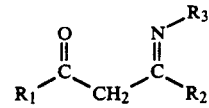

where $R_1 = R_2 = CF_3$, $R_3 = CH_2CF_3$,
$R_1 = CF_2CF_3$, $R_2 = CF_3$, $R_3 = CH_2CF_3$
$R_1 = CF_2CF_2CF_3$, $R_2 = CF_3$, $R_3 = CH_2CF_3$
$R_1 = R_2 = CF_3$, $R_3 = $ phenyl
$R_1 = R_2 = CF_3$, $R_3 = CH_2CH_2OH$ Complexes.

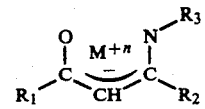

where $R_1 = R_2 = CF_3$, $R_3 = CH_2CF_3$, $M^{+n} = Cu^{+2}$
$R_1 = R_2 = CF_3$, $R_3 = CH_2CF_3$, $M^{+n} = Co^{+2}$
$R_1 = CF_2CF_3$, $R_2 = CF_3$, $R_3 = CH_2CF_3$, $M^{+2} = Cu^{+2}$
$R_1 = CF_2CF_2CF_3$, $R_2 = CF_3$, $R_3 = CH_2CF_3$, $M^{+n} = Cu^{+2}$
$R_1 = R_2 = CF_3$, $R_3 = CH_2CH_2OH$, $M^{+n} = Cu^{+2}$

Experimental

In the following examples, temperatures are set forth uncorrected in degrees Celsius. Unless otherwise indicated, all parts and percentages are by weight.

1,1,1,5,5,5 hexafluoro-2,4-pentanedione, t-butyldimethylsilylchloride, potassium hydride, 2,2,2-trifluoroethylamine, ethylenediamine, ethanolamine, 1,3- propanediamine, 1,3-diamino-2-propanol and analine were obtained from Aldrich Chemical Co. (940 West St. Paul Ave. Milwaukee, Wis. 53233). 1,1,1,2,2,6,6,6-octafluoro-3,5-hexanedione and 1,1,1,2,2,3,3,7,7,7-decafluoro-4,6-heptanedione were obtained from Fairfield Chemical Company Inc. (P.O. Box 20, Blythewood, S.C. 29016).

Solvents used are HPLC grade. Tetrahydrofuran (THF) was distilled from calcium hydride under nitrogen, methanol was distilled from Mg metal under nitrogen. All operations in the preparation of the free ligands or corresponding complexes are carried out using Standard Schlenk line techniques described by D.F. Shriver, "The Manipulation of Air Sensitive Compounds" McGraw-Hill Publishing Co.

Microanalyses were performed by Schwarzkopf Microanalytical Laboratory, Woodside, N.Y. or Research Services, Air Products and Chemicals, Inc. $^1$H, $^{19}$F and $^{13}$C spectra were recorded using an IBM SY-200 and a Bruker WH-200 NMR spectrometer.

The chemical structure, along with both the IUPAC and abbreviated names of the ligands synthesized in the following examples are set out below. The corresponding metal complexes have the similar structure with an (H) being replaced by the metal (see formula II above). The charge on the metal complex must remain neutral, i.e., if the ligand is diprotonated one divalent metal atom such as Cu$^{+2}$ is required.

4-(2,2,2-trifluoroethyl)imino-1,1,1,5,5,5-hexafluoro-2-pentanone
(H)NONO-F[TFEA]

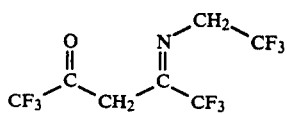

5-(2,2,2-trifluoroethyl)imino-1,1,1,2,2,6,6,6-octafluoro-3-hexanone
(H)UNDECA-F[TFEA]

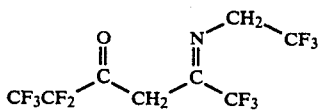

6-(2,2,2-trifluoroethyl)imino-1,1,1,2,
2,3,3,7,7,7-decafluoro-4-heptanone
(H)TRIDECA-F[TFEA]

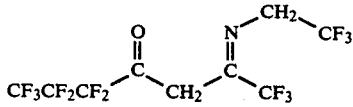

4-(2-hydroxyethyl)imino-1,1,1,5,5,5-hexafluoro-2-pentanone
(H)HEXA-F[EOA]

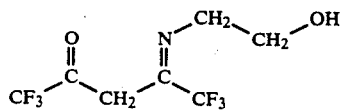

4-(phenyl)imino-1,1,1,5,5,5-hexafluoro-2-pentanone
(H)HEXA-F[AN]

-continued

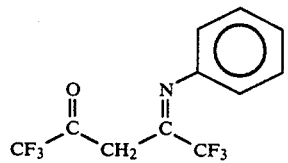

EXAMPLE 1

Synthesis of the Silylenolethers of Perfluorinated β-diketones

The following represents a generic synthesis for the preparation of:
(i) 4-(t-butyldimethylsiloxy)-1,1,1,5,5,5-hexafluoro-3-penten-2-one from 1,1,1,5,5,5-hexafluoro-2,4-pentanediane.
(ii) 4-(t-butyldimethylsiloxy)-1,1,1,5,5,6,6,6 octafluoro-3-hexen-2-one (and its isomer 2-(t-butyldimethylsiloxy)-1,1,1,5,5,6,6,6-octafluoro-2-hexen-4-one) from 1,1,1,5,5,6,6,6-octafluoro-2,4-hexane dione.
(iii) 4-(t-butyldimethylsiloxy)-1,1,1,5,5,6,6,7,7,7-decafluoro-3-hepten-2one (and its isomer 2-(t-butyldimethylsiloxy)-1,1,1,5,5,6,6,7,7,7-decafluoro-2-hepten-4-one) from 1,1,1,5,5,6,6,7,7,7-decafluoro-2-hepten-4-one.

Potassium hydride (20.0 g, 0.5 moles) is charged into a solid addition funnel which is fitted to a 1.01 reaction flask; the latter is also fitted with a rubber septum, an inlet for nitrogen, and a magnetic stir bar. Under an atmosphere of dry nitrogen THF (500 ml) is added to the flask which is subsequently cooled to −78° C. The perfluoro β-diketone (0.5 moles) is then added by syringe to the stirred THF at approx. 0.5 ml/min while also slowly adding potassium hydride at such a rate that it is consumed without an excess accumulating in the reaction flask. After adding all the reagents, the reaction is left to stir at room temperature until all traces of hydride are digested (up to 18 hrs). A reflux condenser and an addition funnel charged with t-butyldimethylsilylchloride (75.36 g. 0.5 moles) are fitted to the reaction flask, 150 ml THF is run into the addition funnel to dissolve the silylchloride. This solution is added dropwise over 30 mins to the stirring reaction mixture after which it is refluxed for 18 hrs. During this time a thick white precipitate of potassium chloride forms. The mixture was then filtered under nitrogen to give a pale brown or yellow filtrate. Approximately 500 ml of THF was then distilled off under nitrogen and the resulting concentrated silylenol ether solution left to cool, thereby precipitating further potassium chloride. This solution was then filtered as before then flash vacuum distilled at ∼70 torr to essentially strip all liquids from residual potassium choride. The pale yellow distillat was then redistilled under nitrogen to give the silylenolether as a moisture sensitive pale yellow liquid.

Each batch of silylenolether collected by distillation showed one major peak >90% purity by gas chromatography. A retention time of 6–7 mins was observed for this peak when using a Supelco ® SPB5 column (30 meter, ID 0.53 mm, 0.25μ film) using a helium flow of 4 ml/min and programmed ith an initial temperature of 50° C. for 5 min floowed by heating at 20° C./min to 200° C. and holding at 200° C. for 5 mins. It is noted that for the silylenolethers that were dstilled over as one fraction composed of two isomers, the gas chromatography conditions described above did not resolve each isomer and so the peak that was observed appeared as if it were of only one component. See Table 1 for analytical data.

mixture is allowed to warm to room temperature and stirred for 1 hr then poured into 400 ml of methanol containing 0.16 moles of potassium methoxide and stirred for 10 minutes. To this bright yellow solution,

TABLE 1

Yields and Analytical Data for Silylenol Ethers

| Starting β-Diketone | Silylenol Ether Formed | Isolated Yield | Boiling Point | NMR |
|---|---|---|---|---|
| 1,1,1,5,5,5-hexafluoro-2,4-pentane dione | 4-(t-butyldimethylsiloxy)-1,1,1,5,5,5-hexafluoro-3-penten-2-one | 64% | 165–175° C. | $^1$H CDCl$_3$ δ0.32(S,6H); δ0.99(S,9H); δ6.27(S,1H) $^{13}$C CDCl$_3$ δ-4.34(S,2C); δ19.20(S,1C) δ25.51(S,3C); δ99.33(S,1C) δ116.0(Q,1C); δ120(Q,1C); δ156.1 (Q,1C); δ178(Q,1C) $^{19}$F CDCl$_3$δ-76.5(S,3F);-70.2(S,3F) |
| 1,1,1,5,5,6,6,6-octafluoro-2,4-pentanedione | 4-(t-butyldimethylsiloxy)-1,1,1,5,5,6,6,6-octafluoro-3-hexen-2-one<br><br>and<br>2-(t-butyldimethylsiloxy)-1,1,1,5,5,6,6,6-octafluoro-2-hexen-4-one<br>(ie. two isomers) | 62%, | 165–175° C. | $^1$H CD$_2$Cl$_2$ δ0.35(S,9H); δ1.0(S,6H); δ6.4(S,1H)<br>(only major isomer shown) |
| 1,1,1,5,5,6,6,7,7,7-decafluoro-2,4-pentanedione | 4-(t-butyldimethylsiloxy)-1,1,1,5,5,6,6,7,7,7-decafluoro-3-hepten-2-one<br><br>and<br>2-(t-butyldimethylsiloxy)-1,1,1,5,5,6,6,7,7,7-2-hepten-4-one<br>(i.e., two isomers) | 49%, | 169–180° C. | $^1$H CD$_2$Cl$_2$ δ0.35(S,9H); δ1.0(S,6H); δ6.4(S,1H)<br>(only major isomer shown) |

EXAMPLE 2

Preparation of Solid Cu$^{+2}$ (NONA-F[TFEA])$_2$, Cu$^{+2}$ (UNDECA-F[TFEA])$_2$. Cu$^{+2}$ (TRIDECA-F[TFEA])$_2$ The above metal complexes are obtained by reaction between 1,1,1-trifluoroethylamine and the silylenolethers of the perfluorinated β-diketones synthesized in Example 1, followed by treatment with copper bromide.

Under a nitrogen atmosphere, 1,1,1-trifluoroethylamine (12.4 ml, 0.16 moles) is added over 5 mins to 0.16 moles of neat silylenol ether cooled to −78° C. This copper bromide (17.1 g, 0.08 moles) is added and the mixture stirred for 1 hour. The potassium bromide precipitate is filtered off, solvent stripped away and the resultant solid twice sublimed under dynamic vacuum to give dark green needles of product complex. The yields and analytical data are reported in Table 2 below.

TABLE 2

Yields and Analytical Data for Cu$^{+2}$(NONA-F[TFEA])$_2$, Cu$^{+2}$(UNDECA-F[TFEA])$_2$, Cu$^{+2}$(TRIDECA-F[TFEA])$_2$

| Starting Enolether | Complex | Yield Isolated Solid | Melting Point | Mass Spec | Elemental Analysis |
|---|---|---|---|---|---|
| CF$_3$–C(=O)–CH=C(O-Si(CH$_3$)$_2$-t-butyl)–CF$_3$ | Cu$^{+2}$(NONA-F[TFEA])$_2$ | 71% | 82–86° C. | cal 638.9438<br>found 638.946 | Cal %: C 26.28;<br>H 0.95; N 4.38;<br>O 5.00; F 53.46;<br>Cu 9.93<br>Found %: C 26.12;<br>H 0.78; N 3.81;<br>O F 50.40;<br>Cu 10.10 |
| CF$_3$CF$_2$–C(=O)–CH=C(O-Si(CH$_3$)$_2$-t-butyl)–CF$_3$ | Cu$^{+2}$(UNDECA-F[TFEA])$_2$ | 77% | 73–75° C. | cal 738.9374<br>found 738.939 | Cal %: C 25.98;<br>H 0.82; N 3.79;<br>O 4.33; F 56.50;<br>Cu 8.59<br>Found %: C 25.53;<br>H 0.66; N 3.95;<br>O F 54.60;<br>Cu 8.56 |
| CF$_3$CF$_2$CF$_2$–C(=O)–CH=C(O-Si(CH$_3$)$_2$-t-butyl)–CF$_3$ | Cu$^{+2}$(TRIDECA-F[TFEA])$_2$ | 63% | 70–73° C. | cal 838.9310<br>found 838.930 | Cal %: C 26.97;<br>H 0.75; N 3.49;<br>O 3.99; F 56.87;<br>Cu 7.93<br>Found %: C 25.57;<br>H 0.55; N 3.49;<br>O F 55.30;<br>Cu 7.47 |

EXAMPLE 3

Preparation of Ligands (H)NONA-F[TFEA], (H)UNDECA-F[TFEA], (H)TRIDECA-F[TFEA]

solid (i.e. $Cu^{+2}$ (HEXA-F[EOA])$_2$, MPt 232° C.). This is treated with HCl to yield (H)HEXA-F[EOA] as a colorless oil. Analytical data is reported in Table 4 below.

TABLE 4

| | Analytical Data for (H)HEXA-F[EOA] | | |
|---|---|---|---|
| Starting Enolether | Alkanolamine | Ligand Formed | NMR |
| 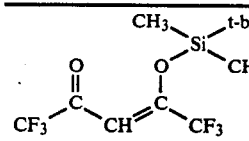 | Ethanolamine | (H)HEXA-F[EOA] | $^1H$ CDCl$_3$ δ2.22(bs,<u>1H</u>);δ3.62(Q,<u>2H</u>); δ3.85(t,<u>2H</u>);δ5.83(S,1H); δ10.8(bs,<u>1H</u>) $^{19}F$ CDCl$_3$ δ − 77.7(S);δ67.7(S) $^{13}C$ CDCl$_3$ δ46.94(S);δ60.29(S); δ85.74(S);δ117.0(Q);δ119.0(Q); δ154(Q);δ179.5(Q) |

A saturated solution of the appropriate parent copper complex (from example 2) in diethyl ether is prepared and washed with excess 50/50 concentrated HCl/H$_2$O. The ether layer is then extracted and treated with more acid until it holds no further green color. The organic layer is then washed with brine, dried over anhydrous sodium sulfate and distilled. Yields of 80–90% of isolated pure colorless ligand were realized. Analytical data is reported in Table 3 below.

EXAMPLE 5

Preparation of Ligand (H)HEXA-F[AN]

Under nitrogen, a 50 ml reaction flask fitted with a reflux condenser is charged with the silylenolether of hexafluoro 2,4-pentanedione (9.66 g, $3 \times 10^{-2}$ moles) and aniline (2.79 g, $3 \times 10^{-2}$ moles) added. The nixture was then refluxed for 35 mins and distilled under vacuum to yield 8.0 g (H)HEXA-F[AN] at 140° C./10 torr

TABLE 3

| | Analytical Data for Ligands (H)NONA-F[TFEA]; (H)UNDECA-F[TFEA]; (H)TRIDECA-F[TFEA] | | |
|---|---|---|---|
| Starting Cu$^{+2}$ Complex | Free Ligand | Elemental Analysis | NMR |
| Cu$^{+2}$(NONA-F[TFEA])$_2$ | (H)NONA-F[TFEA] | Cal %: C 29.07; H 1.39; N 4.85; O 5.53; F 59.15 Found %: C 29.41; H 1.41; N 4.77; O; F 51.70 | $^1H$ CD$_2$Cl$_2$ δ4.07(p,<u>2H</u>); δ6.02(S,<u>1H</u>); δ10.35(bs,<u>1H</u>) $^{19}F$ CDCl$_3$ δ-78.2(S); δ-73.2(m); δ-66.7(m) $^{13}C$ CDCl$_3$ δ46.5(Q); δ89.0(S); δ116.1 (Q); δ118.2(Q); δ122.5(Q); δ133(Q); δ181.4(Q) |
| Cu$^{+2}$ (UNDECA-F[TFEA])$_2$ | (H)UNDECA-F[TFEA] | Cal %: C 28.34; H 1.19; N 4.13; O 4.72; F 61.63 Found %: C 27.76; H 1.04; N 5.35; O; F 58.0 | $^1H$ CDCl$_3$ δ4.0(p,<u>2H</u>); δ6.05(S,<u>1H</u>); δ10.50(bs,<u>1H</u>) $^{19}F$ CDCl$_3$ δ-124(S); δ-83.8(S); δ-74.2(m); δ-67.6(S) $^{13}C$ CDCl$_3$ δ11.2(Q); δ89.7(S);δ107.5 (t); δ118.25(Qt); δ119.0(Q); δ123(Q); δ153.3(Q); δ183.3(t) |
| Cu$^{+2}$ (TRIDECA-F[TFEA])$_2$ | ((H)TRIDECA-F[TFEA]) | Cal %: C 27.78; H 1.04; N 3.60; O 4.11; F 63.47 Found %: C 28.08; H 0.73; N 4.09; O; F 58.0 | $^1H$ CDCl$_3$ δ4.0(hp); δ6.0(S); δ10.5(bs) $^{19}F$ CDCl$_3$ δ-127.8(S); δ-122.5(m); δ-81.8(m); δ74.0(m); δ-67.3(S) $^{13}C$ CDCl$_3$ δ46.43(Q); δ90.12(S); δ108(t,hx); δ109.01(tt); δ117.63(Qt); δ118.92(Q); δ122.87(Q); δ152.9(Q); δ182.9(t) |

EXAMPLE 4

Preparation of Ligands (H)HEXA-F[EOA]

Under a cover of nitrogen, a 100 ml reaction flask fitted with a reflux condenser, addition funnel and magnetic stir bar is charged with the t-butyl dimethylsilylenol ether of hexafluoro-2,4-pentadione (9.66 g, $3 \times 10^{-2}$ moles). The addition funnel is charged with elthanolamine (EOA) (1.83 g, $3.0 \times 10^{-2}$ moles) in 5 ml THF and this solution is then added over 5 mins, with stirring. to the enolether after which the reaction mixture is refluxed 1.5 hrs. The reaction mixture is then poured into excess methanolic copper acetate solution, the entire mixture is extracted with methylene chloride (3×100 ml). The combined organic fractions are washed with water (3×100 ml) then dried over anhydrous sodium sulfate. Removal of solvent yields a blue oil which is chromatographically purified via a Chromatron ® apparatus (Harrison Research, 840 Moana Court, Palo Alto, Calif.) using Kieselgel 60 PF$_{254}$, and CH$_2$Cl$_2$ eluant) to yield a blue crystalline as a yellow liquid.
Yield=94%.
NMR: $^1H$ CDCL$_3$ δ6.05(S,<u>1H</u>); δ7.25(m,<u>2H</u>); δ7.40(m,<u>3H</u>); δ11.90(bS,<u>1H</u>). $^{19}F$ CDCL$_3$ δ—77.8(S); δ—64.1(S). $^{13}C$ neat δ88.0(S); δ117.21(Q); δ119.82(Q); δ126.56(S); δ128.68(S); δ129.45(S); δ136.85(S); δ153.25(Q); δ180.51(Q).

Elemental Analysis: Cal for C$_7$H$_6$NO$_2$F$_6$ % C 33.61; H 2.42; N 5.60; O 12.79; F 45.57. Found: % C 49.31; H 3.68; N 4.15; F 31.0.

EXAMPLE 6

Preparation of a Metal Complex of (H)NONA-F[TFEA]

Under nigrogen, potassium methoxide (1.75 g, 0.025 moles) is dissolved in 150 ml dry methanol and 0.025 moles of a β-iminoketone ligand is added. The mixture is then stirred for 15 minutes to give a clear bright yellow solution. Solid metal dibromide (0.025 moles) is then added and the mixture stirred an additional 1 hour. The mixture is then filtered, the methanol evaporated off from the filtrate and the resultant solide redissolved in toluene (100 ml). This solution is filtered to remove residual potassium bromide and the filtrate evaporated to a solid that is then sublimed under a dynamic vacuum to yield the product complex. The analytical data is as follows:

| | |
|---|---|
| Metal Bromide | = $CoBr_2$ |
| Complex Formed | = $Co^{+2}(NONA\text{-}F[TFEA])_2$ |
| Yield | = 83% |
| M.P. | = 76–77° C. |

Elemental Analysis: Cal for $C_{14}H_6N_2O_2F_{18}CO$: % C 26.48; H 0.95; N 4.41; O 5.04; F 53.84; Co 9.28. Found: % C 25.99; H 0.52; N 4.35; O ; F 45.0; Co 9.51.

EXAMPLE 7

Relative Volatility Measurement of Perfluoro β-ketoiminato Complexes

A standard weight loss experiment for each metal complex was conducted by heating a sample of approximately 50 mg at 10° C./min under a 100 cc/min flow of nitrogen using a DuPont Model No. 951. Thermal Gravimetric Analyzer in conjunction with a model No. 9900 Controller. Table 5 below indicates that all of the metal complexes tested in this way are clearly volatile, leaving as little as 0.34% residue at the end of an evaporation cycle. The data reported indicates that the evaporation of these complexes is a smooth process, i.e. a gradual and even transition from the solid to the gas phase.

TABLE 5

Volatility of Perfluoro β-ketoiminato Copper Complexes

| Complex | Temperature T° C. at which complex is completely vaporized | Residual weight left at T° C. |
|---|---|---|
| $Cu^{+2}(TRIDECA\text{-}F[TFEA])_2$ | 162 | 0.342% |
| $Cu^{+2}(UNDECA\text{-}F[TFEA])_2$ | 157 | 0.652% |
| $Cu^{+2}(NONA\text{-}F[TFEA])_2$ | 150 | 1.81% |

EXAMPLE 8

A run was carried out to react a fluorinated β-diketone with an amine in an attempt to form a β-ketoimine ligand via published procedures that are effective for the condensation of unfluorinated β-diketones or partially fluorinated β-diketones with amines to yield β-ketoimines ligands.

Wallis, et al., (Inorg. Chem. Vol. 13, No. 4. 1974) describe the reaction of 1,1,1-trifluoro-2,4-pentanedione (a partly fluorinated β-diketone) with an amine in methanol solvent to yield a β-ketoimine ligand. The reagents are simply mixed together at 20° C., gently warmed to 30° C. for 30 minutes and the product precipitated by pouring the reaction mixture into water. Similarly, Rugheimer, L. (Ber. 47, 2759, 1914) describes how 2,4-pentanedione (an unfluorinated β-diketone) is successfully reacted with triethylamine to yield a β-ketoimine by cooling 2.1 equivalents of the β-diketone to −21° C., adding one equivalent of the amine, allowing to warm to room temperature then heating for one hour. The authors also note that this reaction can be run using ethanol as solvent.

The following reaction was run to test the viability of the above-synthetic approaches for preparing β-ketoimine ligands from fluorinated β-diketones and amines. Specifically, an attempt was made to prepare a β-ketoimine ligand from 1,1,1,5,5,5-hexafluoro-2,4-pentanedione and ethylamine as follows:

Ethylamine (1.3 ml., 0.9 g, 0.02 moles) were dissolved in 10 ml of absolute ethanol and cooled to 0° C. 1,1,1 5,5,5-hexafluoro-2,4-pentanedione (2.82 ml, 4.16 g, 0.02 moles) were dissolved in 10 ml of absolute ethanol and slowly added to the ethylamine solution over a period of five minutes with stirring. After stirring at 0° C. for fifteen minutes. the solution was allowed to warm to room temperature, then refluxed for one hour. Gas chromatographic analysis of the resultant reaction mixture indicated one major product identified as the hexafluoroacetylacetonate salt of ethylamine. Only a trace of the desired ketoimine ligand was found (identified by mass spectroscopy) representing less than 0.1% of the reaction mixture; that is, present in a sufficiently low quantity as to preclude this synthetic route as being a viable means to prepare this compound.

EXAMPLE 9

A run was carried out in an attempt to reproduce the work of Richardson and Sievers for the synthesis of the ligand

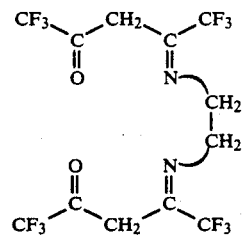

as described in J.Inoro. Nucl. Chem. 1970. vol. 32, p.1895 to 1906.

4.16 g (0.02 moles) of 1,1,1,5,5,5-hexafluoro-2,4-pentanedione were dissolved in 10 ml of benzene and to this solution 0.60g (0.01 mole) of ethylenediamine dissolved in 10 ml benzene were slowly added, with stirring, over a period of five minutes. A cream colored precipitate slowly formed and heat was evolved. The mixture was then boiled and filtered hot. The resulting white precipitate was then washed with hot benzene, refiltered and left to air dry. Yield=4.4 g white solid. To check if any ligand may have formed at this point, the white solid was analyzed by Gas Chromatography (using a Hewlett Packard 5880A gas chromatograph). In this determination an acetone solution of the white salt was shown to contain none of the desired ligand (by comparison to results obtained for the analysis of pure authentic ligand; i.e., $H_2$—DODECA—F[EDA] as obtained via the silylenolether route as described in this patent disclosure). The white salt was then heated under vacuum in a sublimator to 90° C. whereupon the apparatus was sealed shut and the sublimation process allowed to occur. The temperature of the cooling water was set at 16 C. After two hours, a fine powdery film had formed upon the cold finger of the sublimator. This did not bear a strong resemblance to the "large shiny white feathery needles" described by Richardson and Sievers. Gas chromatographic analysis of this solid film showed that it contained no $H_2$—DODECA—F[EDA] ligand. The cold finger of the sublimator was then cleaned, the apparatus reassembled and the sublimation process reinitiated under the same conditions as before allowing two hours of sublimation time. Again, a white film appeared on the cold finger. Gas chromatographic analysis of this solid indicated a total absence of $H_2$—DODE-CA—F[EDA] ligand.

Having thus described the present invention, what is now deemed appropriate for Letters Patent in set out in the following appended claims.

What is claimed is:

1. A thermally volatilizable, $\beta$-ketoiminato metal complex having the structural formula:

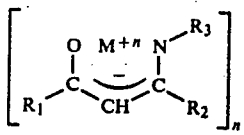

wherein $R_1$ and $R_2$ are independently linear or branched, perfluorinated, $C_1$-$C_8$ alkyl groups, $R_3$ is an unfluorinated, partially fluorinated or fully fluorinated phenyl or $C_1$-$C_8$ alkyl, hydroxyalkyl or ether group, M is a metal which is capable of forming a complex with a ligand as shown above, and n=1, 2 or 3.

2. A metal complex in accordance with claim 1 wherein both $R_1$ and $R_2$ are $CF_3$.

3. A metal complex in accordance with claim 1 wherein $R_1$ and $R_2$ are independently perfluorinated methyl, ethyl or propyl groups.

4. A metal complex in accordance with claim 3 wherein $R_3$ is $CH_2CF_3$.

5. A metal complex in accordance with claim 1 wherein $M^{+n}$ is $Cu^{+2}$.

6. A metal complex in accordance with claim 1 wherein $M^{+n}$ is $Co^{+2}$.

7. A process for making a thermally volatizable, $\beta$-ketoiminato metal complex having the structural formula:

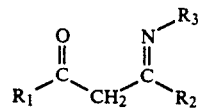

wherein $R_1$ and $R_2$ are independently linear or branched, perfluorinated, $C_1$-$C_8$ alkyl groups, $R_3$ is an unfluorinated, partially fluorinated or fully fluorinated phenyl or $C_1$-$C_8$ alkyl, hydroxyalkyl or ether group, M is a metal which is capable of forming a complex with a ligand as shown above, and n=1, 2 or 3, said process comprising:

(a) treating a $\beta$-diketone of the formula $R_1COCH_2COR_2$ with potassium hydride under anhydrous conditions to produce a compound of the formula $R_1COCHCOR_2^-K^+$;

(b) treating the resultant $R_1COCHCOR_2^-K^+$ with a silylchloride of the formula $(R_5)_3SiCl$, wherein each $R_5$ is independently an alkyl group, to produce a silylenolether of the formula

wherein $R_1$, $R_2$ and $R_5$ are as above;

(c) treating said silylenolether with a primary monoamine of the formula $R_3NH_2$ wherein $R_3$ is as described above to produce the desired $\beta$-ketoimine ligand;

(d) treating the $\beta$-ketoimine ligand produced in step (c) with potassium methoxide to produce a comopund of the formula $R_1COCHCN(R_3)R_2^-K^+$ wherein $R_1$, $R_2$ and $R_3$ are as above; and (e) subsequently treating the compound formed in step (d) with a metal halide of the formula $M^{+n}(X)_n$, wherein N=1, 2 or 3 X is a halogen, to form the desired metal complex.

* * * * *

UNITED STATES PATENT AND TRADEMARK OFFICE
CERTIFICATE OF CORRECTION

PATENT NO. : 5,008,415
DATED : April 16, 1991
INVENTOR(S) : John A. T. Norman

It is certified that error appears in the above-identified patent and that said Letters Patent is hereby corrected as shown below:

Column 14, Lines 1 - 5, first figure
   Delete in its entirety and substitute therefor -- 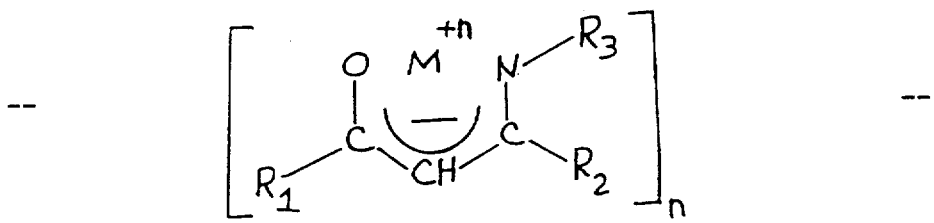 --

Signed and Sealed this

Sixth Day of October, 1992

*Attest:*

DOUGLAS B. COMER

*Attesting Officer*   Acting Commissioner of Patents and Trademarks